(12) United States Patent
Schwinn et al.

(10) Patent No.: US 7,592,141 B2
(45) Date of Patent: Sep. 22, 2009

(54) METHODS OF IDENTIFYING INDIVIDUALS AT REDUCED RISK OF SEPSIS

(75) Inventors: Debra A. Schwinn, Durham, NC (US); Daniel Laskowitz, Chapel Hill, NC (US); Mihai V. Podgoreanu, Raleigh, NC (US); Eugene W. Moretti, Durham, NC (US)

(73) Assignee: Duke University, Durham, NC (US)

( * ) Notice: Subject to any disclaimer, the term of this patent is extended or adjusted under 35 U.S.C. 154(b) by 284 days.

(21) Appl. No.: 11/302,064

(22) Filed: Dec. 13, 2005

(65) Prior Publication Data

US 2006/0177848 A1    Aug. 10, 2006

Related U.S. Application Data

(60) Provisional application No. 60/635,181, filed on Dec. 13, 2004.

(51) Int. Cl.
*C12Q 1/68* (2006.01)
*C12P 19/34* (2006.01)
*C12M 1/34* (2006.01)
*C07H 21/04* (2006.01)

(52) U.S. Cl. .......................... 435/6; 435/91.1; 435/91.2; 435/287.1; 536/24.31; 536/24.33

(58) Field of Classification Search .................. None
See application file for complete search history.

(56) References Cited

FOREIGN PATENT DOCUMENTS

| WO | WO 95/16791 | * | 6/1995 |
| WO | WO 03/060158 | * | 7/2003 |

OTHER PUBLICATIONS

Harris HW, Crit Care Med 2005 vol. 33, No. 11, p. 2696-2697.*
Juppner H, Bone vol. 17, No. 2, Supplement Aug. 1995:39S-42S.*
Lucentini J, The Scientist, vol. 18, Issue 24, p. 20.*
Moretti EW et al, Crit Care Med 2005 vol. 33, No. 11 p. 2521-2526.*
Hegele RA, Arterioscler Thromb Vasc Biol., 2002, vol. 22, p. 1058-1061.*
Wu G et al, Br J Haematol. Jul. 2003;122(2):311-6.*
Wang H. et al. 'APOE genotype affects outcome in a murine model of sepsis: implications for a new treatment strategy.' Anaesth Intensive Care (Jan. 2009) vol. 37, No. 1, pp. 38-45. (Abstract only provided, 2 printed pages).*

* cited by examiner

*Primary Examiner*—Stephen Kapushoc
(74) *Attorney, Agent, or Firm*—Myers Bigel Sibley & Sajovec, P.A.

(57) ABSTRACT

The present invention provides a method of identifying a subject having a reduced risk of developing sepsis, comprising detecting at least one APOE3 allele in nucleic acid from the subject.

16 Claims, 3 Drawing Sheets

METHODS OF IDENTIFYING INDIVIDUALS AT REDUCED RISK OF SEPSIS

CROSS REFERENCE TO RELATED APPLICATIONS

This application claims the benefit, under 35 U.S.C. § 119(e) of U.S. Provisional Application Ser. No. 60/635,181, filed Dec. 13, 2004, the disclosure of which is incorporated herein by reference in its entirety.

STATEMENT OF GOVERNMENT SUPPORT

This invention was made with government support under grant numbers 5R21 NS044870 and R01 AG17556 from the National Institutes of Health. The United States Government has certain rights in this invention.

FIELD OF THE INVENTION

The present invention relates, in general, to sepsis and, in particular, to methods of identifying individuals at reduced risk of sepsis associated with a robustly stressful event (e.g., perioperative and/or periprocedural sepsis).

BACKGROUND OF THE INVENTION

Sepsis syndrome arises from a systemic inflammatory response syndrome (SIRS) initiated by an infectious insult. Of approximately 751,000 cases of sepsis syndrome that occur annually in the United States, 35-45% of patients who experience this syndrome die (Angus et al., *Crit. Care Med.* 29(7):1303-1310 (2001); *Crit. Care Med.* 20(6):864-874 (1992)). While precise mechanisms leading to organ dysfunction mediated by SIRS and sepsis remain incompletely understood (Levy et al., *Crit. Care Med.* 31(4):1250-1256 (2003), Bone, *Crit. Care Med.* 24(1):163-172 (1996), Goldie et al., *JAMA* 274(2):172-177 (1995), Rangel-Frausto et al., *JAMA* 273(2):117-123 (1995), recent evidence suggests a novel role for lipid mediators (Alvarez and Ramos, *Clin. Chem.* 32(1 Pt 1):142-145 (1986), van Leeuwen et al., *Crit. Care Med.* 31(5):1359-1366 (2003), Fraunberger et al., *Schok* 10(5): 359-363 (1998), Gordon et al., *Crit. Care Med.* 24(4):584-589 (1996)).

Lipid profile alterations have been reported in many acute inflammatory processes (Alvarez and Ramos, *Clin. Chem.* 32(1 Pt 1):142-145 (1986)). Recently, an inverse correlation was described between tumor-necrosis factor alpha (TNF α) and lipid components (van Leeuwen et al., *Crit. Care Med.* 31(5):1359-1366 (2003), Fraunberger et al., *Schok* 10(5): 359-363 (1998), Gordon et al., *Crit. Care Med.* 24(4):584-589 (1996)). Apolipoprotein E (apoE protein; APOE gene) is a 34 kDa protein originally studied for its role in cholesterol metabolism. Independent of its role in cholesterol metabolism, apoE modulates innate and acquired immune responses in vitro and in vivo (Laskowitz et al., *J. Lipid Res.* 41(4):613-620 (2000)). ApoE deficient animals have impaired immunity after bacterial challenge, and they also have increased susceptibility to endotoxemia after intravenous lipopolysaccharide (LPS) administration (Roselaar and Daugherty, *J. Lipid Res.* 39(9):1740-1743 (1998), de Bont et al., *J. Lipid Res.* 40(4):680-685 (1999)). ApoE deficient animals also have been reported to have an increased systemic inflammatory response and higher mortality following LPS injection, and administration of exogenous apoE improved mortality by down regulating the inflammatory cascade (Van Ooosten et al., *J. Biol. Chem.* 276(12):8820-8824 (2001)).

There are three common human isoforms of apoE, designated E2, E3 and E4, encoded for by three alleles at the APOE locus on human chromosome 19 (Weisgraber, *Adv. Protein Chem.* 45:249-302 (1994)). These isoforms differ by single amino acid interchanges at residues 112 and 158: E3 ($Cys_{112}$ $Arg_{58}$); E4 ($Arg_{112}$ $Arg_{158}$); and E2 ($Cys_{112}$ $Cys_{158}$) (Weisgraber, *Adv. Protein Chem.* 45:249-302 (1994)). Isoform-specific differences in immune regulation have been described for apoE, and may play a pivotal role in mediating the CNS and systemic response to injury. For example, a recent preclinical study demonstrated that mice expressing the human APOE4 gene have enhanced systemic and CNS inflammatory responses following lipopolysaccharide (LPS) injection, as compared to their APOE3 counterparts (Curtiss and Edgington, *J. Immunol.* 126(4):1382-1386 (1981)). In addition, the apoE4 protein has been shown to be less effective than apoE3 or apoE2 at suppressing the activation of microglia in cell culture models of brain inflammation (Barger and Harmon, *Nature* 388(6645):878-881 (1997), Laskowitz et al., *Exp. Neurol.* 167(1):74-85 (2001)). Indeed the APOE4 allele has been associated with the early onset of Alzheimer's disease and poor prognosis in multiple sclerosis (Strittmatter and Roses, *Annu. Rev. Neurosci.* 19:53-77 (1996), Schmidt et al., *Am. J Hum. Genet.* 70(3):708-717 (2002)), as well as poor prognosis following traumatic brain injury, and with an increase in the systemic inflammatory response following cardiopulmonary bypass (Sorbi et al., *Nat. Med.* 1(9):852 (1995), Friedman et al., *Neurology* 52(2): 244-248 (1999), Grocott et al., *J. Thorac. Cardiovasc. Surg.* 122(3):622-623 (2001)).

The present invention overcomes previous shortcomings in the art by providing methods of identifying individual having a reduced risk of sepsis.

SUMMARY OF THE INVENTION

The present invention provides a method of identifying a subject having a decreased risk of developing sepsis, comprising detecting at least one copy of an APOE3 allele in nucleic acid of the subject.

Objects and advantages of the present invention are described in the description that follows.

DETAILED DESCRIPTION OF THE INVENTION

Figure 1:
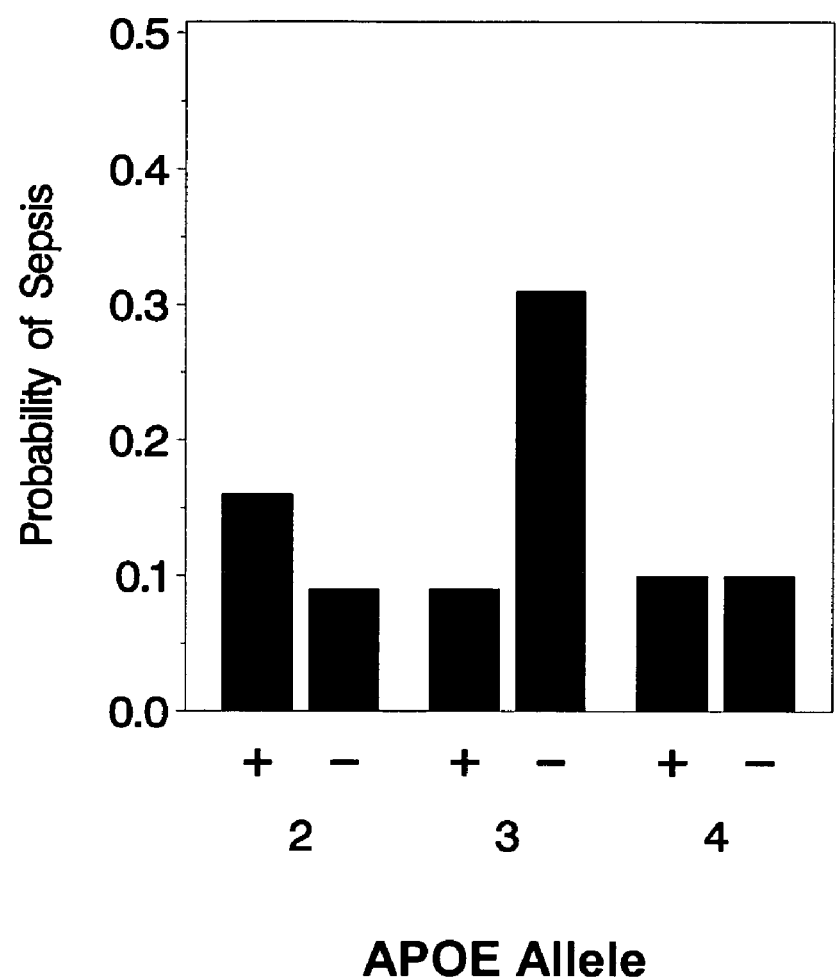
FIG. 1. Estimates of probability of sepsis for APOE genotypes defined by presence (+) or absence (−) of APOE alleles 2, 3 or 4.

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention is based on the unexpected discovery of a correlation between sepsis risk and a genetic marker. In particular, these studies demonstrate that the APOE3 allele is significantly associated with a decreased risk of developing sepsis. The present invention provides a definitive association between this APOE allele and the development of sepsis. The invention is exemplified by reference to non-cardiac surgery patients but includes all perioperative, periprocedure (endoscopy, bronchoscopy, cardiac catheterization, non-surgical trauma, etc.), and intensive care unit settings, as set forth below.

Thus, in one aspect, the present invention provides a method of identifying a subject having a decreased risk of developing sepsis, comprising detecting at least one copy of an APOE3 allele in nucleic acid of the subject.

The subject of this invention is any animal susceptible to developing sepsis that carries an APOE gene, which can be a mammal, such as a domestic and/or commercially important mammal (e.g., dog, cat, horse, cow, sheep, goat, rabbit, mouse, rat, etc.) and which in particular embodiments is a human.

In some embodiments of this invention, the subject of this invention is a subject that has experienced a major or robustly stressful event that can increase the likelihood of the development of sepsis in the subject, as would be known to one of skill in the art. Nonlimiting examples of this type of stressful event can include placement in a hospital or other medical facility, an elective surgery, a non-elective surgery, an elective invasive procedure, a non-elective invasive procedure, trauma or injury to the subject (e.g., automobile accident or other accidental trauma or injury) and/or any disease condition or pathological state that can increase the likelihood of development of sepsis in the subject, as would be well known to one of skill in the art.

Thus, in particular embodiments of the invention, the subject can be a perioperative patient, a postoperative patient, a preoperative patient, a periprocedural patient, a postprocedural patient, a preprocedural patient, an intensive care unit patient, a post-intensive care unit patient, a trauma patient, an acutely ill patient, a chronically ill patient and any combination of the above.

In other words, subject of this invention can be a subject who is about to undergo a surgery and/or invasive procedure, a subject who is preparing to undergo a surgery and/or invasive procedure and/or a subject who is about to undergo and/or is preparing to undergo a medical treatment that can increase the likelihood of the development of sepsis in the subject. In some embodiments, the subject of this invention can be a subject who has undergone a surgery and/or invasive procedure and/or a subject who has undergone a medical treatment that can increase the likelihood of development-of sepsis in the subject. Furthermore, the subject of this invention can be a subject who is about to receive and/or who has received medical treatment that does result and/or could result in placement of the subject in an intensive care unit.

As used herein, "perioperative and periprocedural" mean the period of time extending from when the subject goes into a hospital, clinic, doctor's office or other facility for surgery, a procedure and/or other medical treatment until the time the subject returns home. Accordingly, preoperative and preprocedural means the period of time before the subject goes into a hospital, clinic, doctor's office or other facility for surgery, a procedure and/or other medical treatment and postoperative and postprocedure means the period of time after the subject returns home following the surgery, procedure and/or other medical treatment.

Furthermore, as used herein, "an intensive care unit patient" is a subject who has been admitted to an intensive care unit of a hospital, clinic or other medical facility for any medical condition that warrants intensive care, as would be known by one of skill in the art. A "post-intensive care unit patient" is a subject who had previously been cared for in an intensive care unit of a hospital, clinic or other medical facility and has been discharged from the intensive care unit.

Also as used herein, the term "invasive procedure" means any technique where entry to a body cavity is required or where the normal function of the body is in some way interrupted. An invasive procedure can also be a medical procedure and/or treatment that invades (enters) the body, usually by cutting or puncturing the skin or by inserting instruments into the body.

Nonlimiting examples of an invasive procedure of this invention include endoscopy, bronchoscopy, cardiac catheterization, angioplasty, colonoscopy and any combination thereof.

In addition, nonlimiting examples of a surgery, operation or surgical procedure of this invention include surgery of an, organ or tissue (e.g., heart, lung, stomach, kidneys, uterus, ovaries, intestines, colon, brain, prostate, gall bladder, appendix, joint, etc.) and can include transplantation of organs and/or tissue (e.g., bone marrow, skin graft, kidney, liver, heart, cornea, etc.), removal of organs, bariatric surgery, laparoscopic surgery, hernia surgery, hemorrhoid surgery, plastic surgery, exploratory surgery, varicose vein surgery, minimally invasive surgery, etc.

In some embodiments of the methods of this invention, the subject of this invention can have one copy of the APOE allele and in some embodiments, the subject of this invention can have two copies of the APOE3 allele.

It is further contemplated that the methods of this invention can be carried out at any time relative to the major stress event that increases the likelihood of development of sepsis in the subject. Thus, the methods of this invention can be carried out prior to, during and/or after surgery, an invasive procedure, a trauma or injury and/or a treatment that increases the likelihood of sepsis. The methods can also be carried out prior to, during and/or after a subject is a patient in an intensive care unit.

In further embodiments, the methods of this invention can be carried out on a subject who has developed sepsis, including a current sepsis, as well as a past incident of sepsis from which the subject has recovered. In additional embodiments, the subject can have a relative (e.g., parent, sibling, aunt, uncle, grandparent, niece, nephew, etc.) who has developed sepsis, which can be a current sepsis and/or a past incident of sepsis.

An association study of the presence of an APOE3 allele in a subject and a decrease in the subject's risk of developing sepsis involves determining the presence or frequency of the APOE alleles in a biological sample from individuals who have developed sepsis under the various conditions described herein (e.g., after experiencing a major stress event, perioperative, periprocedural and/or in the intensive care unit) and comparing the information to -that of controls (i.e., individuals who do not have sepsis; controls may be also referred to as "healthy" or "normal" individuals) who are preferably of similar age and race and/or have the same condition (e.g., after experiencing a major stress event, perioperative, periprocedural and/or in the intensive care unit). The appropriate selection of patients and controls is important to the success of the association studies.

An allele of the APOE gene is correlated with an increased or decreased risk of developing sepsis by identifying the presence of a particular APOE allele in the nucleic acid of subjects also identified as having sepsis and in nucleic aid of subjects identified as not having sepsis and performing a statistical analysis of the association of the APOE allele with the presence or absence of sepsis in the subject, according to well known methods of statistical analysis. An analysis that identifies a statistical association (e.g., a significant association) between the particular APOE allele and the presence or absence of sepsis establishes a correlation between the presence of the APOE allele in a subject and an increased or decreased risk of developing sepsis.

To conduct these studies, an APOE allele is identified in any nucleic acid-containing biological sample from a subject diagnosed with sepsis, and compared to the APOE allele present in control samples, and selected for its increased (or decreased) occurrence in a specific phenotype, such as presence or absence of sepsis under the conditions described herein. Statistical analyses are then conducted to identify a statistically significant association between an APOE allele and the presence or absence of sepsis (e.g., as described in the EXAMPLES section herein and as is otherwise known in the art).

The methods of this invention can also be used to identify subjects most suited to therapy with particular pharmaceutical agents, e.g., to prophylactically treat a subject at increased risk of developing sepsis. Thus, the present invention further provides a method of identifying a patient in need of prophylactic treatment for sepsis, comprising detecting an APOE allele in the subject that is not APOE3. Similarly, the identification of an APOE allele in a subject can be used to exclude patients from certain surgeries, procedures and/or treatments due to the patient's increased likelihood of developing sepsis. Thus, in further embodiments, the present invention provides a method of identifying a subject who is not suitable for surgery, an invasive procedure and/or a treatment that increases the likelihood of the development of sepsis in the subject, comprising detecting an APOE allele in the subject that is not APOE3. The methods of this invention can also be employed in other pharmacogenomics analyses to assist the drug development and selection process. (Linder et al. (1997) *Clinical Chemistry* 43:254; Marshall (1997) *Nature Biotechnology* 15:1249; International Patent Publication No. WO 97/40462; Schafer et al. (1998) *Nature Biotechnology* 16:3).

In particular, preoperative screening for the APOE genotype of a subject enables clinicians to better stratify a given patient for therapeutic intervention, either with drug therapy or with other modalities. Additionally, knowledge of APOE genotype allows patients to choose, in a more informed way in consultation with their physician, medical versus procedural therapy. Identifying APOE genotype of patients who decide to or must undergo surgery or other invasive procedures enables health care providers to design altered therapeutic strategies aimed at preventing the incidence of sepsis in patients without the protective APOE3 allele. In addition, identifying the APOE genotype in patients who have already experienced sepsis, or who have a relative develop sepsis, might also lead to alteration or modification in the therapeutic strategy so as to be more aggressive and proactive.

As indicated above, preoperative and/or preprocedural genotype testing can refine risk stratification and improve patient outcome. Based on the genetic risk factors identified, drugs already available and used to minimize the risk of sepsis (e.g., antibiotics) can be useful in reducing sepsis risk in acute settings, for example, cardiac or non-cardiac surgery. APOE genotyping can facilitate individually tailored medical therapy (personalized medicine) designed to reduce sepsis risk and associated morbidity and mortality. Perioperative screening can facilitate alterations in the usual course of the surgical procedure with institution of procedures designed to additionally reduce this risk.

The identification of an APOE allele in a sample (e.g., a biological sample such as blood, cells or tissue) can be determined using any of a variety of genotyping techniques known in the art, as described below. The invention further provides kits suitable for use in identifying an APOE allele in a nucleic acid. Such kits can include, for example, reagents (e.g., probes or primers) necessary to effect APOE genotyping, as are well known in the art.

In carrying out the methods of this invention, detection reagents can be developed and used to identify any allele of the present invention individually or in combination with the identification of other alleles, and such detection reagents can be readily incorporated into one of the established kit or system formats that are well known in the art. The terms "kits" and "systems," as used herein refer, e.g., to combinations of multiple allele detection reagents, or one or more allele detection reagents in combination with one or more other types of elements or components (e.g., other types of biochemical reagents, containers, packages such as packaging intended for commercial sale, substrates to which allele detection reagents are attached, electronic hardware components, etc.) Accordingly, the present invention further provides allele detection/identification kits and systems, including but not limited to, packaged probe and primer sets (e.g., TAQMAN probe/primer sets), arrays/microarrays of nucleic acid molecules, and/or beads that contain one or more probes, primers, or other detection reagents for detecting/identifying one or more alleles of the present invention. The kits/systems can optionally include various electronic hardware components; for example, arrays ("DNA chips") and microfluidic systems ("lab-on-a-chip" systems) provided by various manufacturers. Other kits/systems (e.g., probe/primer sets) may not include electronic hardware components, but can be comprised of, for example, one or more detection reagents (along with, optionally, other biochemical reagents) packaged in one or more containers.

In some embodiments, a kit of this invention typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, etc.) necessary to carry out an assay or reaction, such as amplification and/or detection of an allele-containing nucleic acid molecule. In some embodiments of the present invention, kits are provided that contain the necessary reagents to carry out one or more assays to detect one or more alleles disclosed herein. In some embodiments of the present invention, allele detection kits/systems are in the form of nucleic acid arrays, or compartmentalized kits, including microfluidic/lab-on-a-chip systems.

Allele detection kits/systems of this invention can contain, for example, one or more probes, or pairs of probes, that hybridize to a nucleic acid molecule at or near each target allele position. Multiple pairs of allele-specific probes can be included in the kit/system to simultaneously assay large numbers of alleles, at least one of which is an allele of the present invention. In some kits/systems, the allele-specific probes can be immobilized to a substrate such as an array or bead. The terms "arrays," "microarrays," and "DNA chips" are used herein interchangeably to refer to an array of distinct polynucleotides affixed to a substrate, such as glass, plastic, paper, nylon and/or other type of membrane, filter, chip, and/or any other suitable solid support. The polynucleotides can be synthesized directly on the substrate, or synthesized separate from the substrate and then affixed to the substrate. In one embodiment, the microarray can be prepared and used according to the methods described in U.S. Pat. Nos. 5,837,832, 5,807,522, PCT publication no. WO 95/11995, Lockhart et al. (1996) Nat. Biotech. 14:1675-1680; and Schena et al. (1996) Proc. Natl. Acad. Sci. 93:10614-10619, all of which are incorporated herein in their entireties by reference.

Any number of probes, such as allele-specific probes, can be implemented in an array, and each probe or pair of probes can hybridize to a different allele position. Polynucleotide probes can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A microarray can be composed of a large number of unique, single-stranded polynucleotides, usually either synthetic antisense polynucleotides or fragments of cDNAs fixed to a solid support. Typical polynucleotides can be about 6-601 nucleotides in length in some embodiments, about 15-30 nucleotides in length in other embodiments, and about 18-25 nucleotides in length in yet other embodiments of this invention. For certain types of microarrays or other detection kits/systems, oligonucleotides that are only about 7-20 nucleotides in length can be used. In other types of arrays, such as arrays used in conjunction with chemiluminescence detection technology, probe lengths can be, for example, about 15-80 nucleotides, about 50-70 nucleotides in length, about 55-65 nucleotides in length, and/or about 60 nucleotides in length. The microarray or detection kit can contain polynucleotides that cover the known 5' or 3' sequence of a gene/transcript or target allele site, sequential polynucleotides that cover the full-length sequence of a gene/transcript; and/or unique polynucleotides selected from particular areas along the length of a target gene/transcript sequence.

Hybridization assays based on polynucleotide arrays rely on the differences in hybridization stability of the probes to perfectly matched and mismatched target sequence variants. For SNP genotyping, stringency conditions used in hybridization assays can be high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions can be used, for example, in nucleic acid arrays of allele-specific probes for SNP detection. Such, high stringency conditions are well known to those skilled in the art and can be found in, for example, Current Protocols in Molecular Biology, John Wiley & Sons, N.Y. (1989), 6.3.1-6.3.6.

In other embodiments, the arrays are used in conjunction with chemiluminescence detection technology, as is known in the art (see, e.g. U.S. Pat. Nos. 6,124,478, 6,107,024, 5,994,073, 5,981,768, 5,871,938, 5,843,681, 5,800,999, and 5,773,628, which describe methods and compositions for performing chemiluminescence detection; and U.S. patent publication no. 2002/0110828, which discloses methods and compositions for microarray controls. All of these references are incorporated herein in their entireties by reference.).

A polynucleotide probe can be synthesized on the surface of the substrate by using a chemical coupling procedure and an ink jet application apparatus, as described, for example, in PCT publication no. WO 95/251116, which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical and/or chemical bonding procedures. An array, such as described above, can be produced by hand or by using available devices (slot blot or dot blot apparatus), materials (any suitable solid support), and/or machines (including robotic instruments), and may contain: 8, 24, 96, 384, 1536, 6144 or more polynucleotides, or any other number which lends itself to the efficient use of commercially available instrumentation.

Using such arrays and/or other kits/systems, the present invention provides methods of identifying the alleles disclosed herein in a biological test sample. Such methods typically involve incubating a sample containing nucleic acid with an array comprising one or more probes corresponding to at least one allele of the present invention, and assaying for binding of a nucleic acid from the test sample with one or more of the probes. Conditions for incubating a detection reagent (or a kit/system that employs one or more such detection reagents) with a test sample vary. Incubation conditions depend on such factors as the format employed in the assay, the detection methods employed, and/or the type and nature of the detection reagents used in the assay. One skilled in the art will recognize that any one of the commonly available hybridization, amplification and array assay formats can readily be adapted to detect the alleles disclosed herein.

A detection kit/system of the present invention can include components that are used to prepare nucleic acids from a test sample for the subsequent amplification and/or detection of an allele-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue specimens. The test samples used in the above-described methods will vary based on such factors as the assay format, nature of the detection method, and the specific tissues, cells or extracts used as the test sample to be assayed. Methods of preparing nucleic acids, proteins, and cell extracts are well known in the art and can be readily adapted to obtain a sample that is compatible with the system utilized. Automated sample preparation systems for extracting nucleic acids from a test sample are commercially available (e.g., Qiagen's BIOROBOT 9600, Applied Biosystems' PRISM 6700, and Roche Molecular Systems COBAS AmpliPrep System).

Another form of kit included in the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more SNPs of the present invention, one or more containers which contain wash reagents (such as phosphate buffered saline, Tris-buffers, etc.), and one or more containers which contain the reagents used to reveal the presence of the bound probe or other SNP detection reagents. The kit can optionally further comprise compartments and/or reagents for, for example, nucleic acid amplification or other enzymatic reactions such as primer extension reactions, hybridization, ligation, electrophoresis (preferably capillary electrophoresis), mass spectrometry, and/or laser-induced fluorescent detection. The kit can also include instructions for using the kit. Exemplary compartmentalized kits include microfluidic devices known in the art (e.g., Weigl et al. (2003) "Lab-on-a-chip for drug development" *Adv Drug Deliv Rev.* 55(3):349-77). In such microfluidic devices, the containers may be referred to as, for example, microfluidic "compartments," "chambers," or "channels."

Microfluidic devices, which may also be referred to as "lab-on-a-chip" systems, biomedical micro-electro-mechanical systems (bioMEMs), or multicomponent integrated systems, are exemplary kits/systems of the present invention for analyzing alleles. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more alleles of the present invention. One example of a microfluidic system is disclosed in U.S. Pat. No. 5,589,136, which describes the integration of PCR-amplification and capillary electrophoresis in chips and which is incorporated by reference herein in its entirety. Exemplary microfluidic systems comprise a pattern of microchannels designed onto a glass, silicon, quartz, or plastic wafer included on a microchip. The movements of the samples can be controlled by electric, electroosmotic or hydrostatic forces applied across different areas of the microchip to create functional microscopic valves and pumps with no moving parts. Varying the voltage can be used as a means to control the liquid flow at intersections between the micro-machined channels and to change the liquid flow rate for pumping across different sections of the microchip. See, for example, U.S. Pat. No. 6,153,073, Dubrow et al., and U.S. Pat. No. 6,156,181, Parce et al.

For genotyping alleles of this invention, an exemplary microfluidic system may integrate, for example, nucleic acid amplification, primer-extension, capillary electrophoresis, and a detection method such as laser induced fluorescence detection. In a first step of such an exemplary system, nucleic acid samples are amplified, preferably by PCR. Then, the amplification products are subjected to automated primer extension reactions using ddNTPs (specific fluorescence for each ddNTP) and the appropriate oligonucleotide primers to carry out primer extension reactions that hybridize just upstream of the targeted allele. Once the extension at the 3' end is completed, the primers are separated from the unincorporated fluorescence ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. Such an exemplary microchip can be used to process, for example, at least 96 to 384 samples, or more, in parallel.

As noted above, any of a variety of suitable techniques can be employed in the methods of this invention for detection of an allele of this invention. Such techniques can include, for example, the use of restriction fragment length polymorphism (RFLP) analysis, mass spectrometry (see also Ye et al., *Hum. Mutat.* 17(4):305 (2001), Chen et al., *Genome Res.* 10:549 (2000)), nanotechnology protocols for genomic characterization and any other protocol or technique now known or later for use in identifying genomic characteristics, including any of a variety of single nucleotide polymorphism (SNP) detection techniques now known or later developed.

In particular, for the identification of single-nucleotide polymorphisms (SNPs) in nucleic acid, various methods can be used, including, but not limited to, fluorescence-based sequencing, hybridization high-density variation-detection DNA chips, high performance liquid chromatography, allele-specific oligonucleotide hybridization (ASOH), nick translation PCR, PCR-ELISA ASO typing, dynamic allele-specific hybridization (DASH), allele-specific inverse PCR (ASIP), inverse PCR-RFLP (IP-RFLP), single stranded conformational polymorphism (SSCP) genotyping, bi-directional PCR amplification of specific allele (bi-PASA), high-throughput SNP genotyping, homogeneous allele-specific PCR based SNP genotyping, molecular inversion probe genotyping, amplification refractory mutation system (ARMS), locked nucleic (LN) SNP genotyping, molecular beacon sequence analysis, high performance multiplex SNP analysis, amplified fragment length polymorphism (AFLP), melting curve analysis of SNPs, tetra-primer ARMS-PCR, ligase chain reaction, allele-specific polymerase chain reaction; $T_m$ shift genotyping, and minisequencing.

In a particular embodiment, the present invention provides a primer pair for detecting an APOE3 allele in a nucleic acid sample, wherein the primer pair consists of an oligonucleotide comprising the nucleotide sequence 5'TAAGCTTG-GCACGGCTGTCCAAGGA3' (SEQ ID NO:1) and an oligonucleotide comprising the nucleotide sequence 5'ACAGAATTCGCCCCGGCCTGGTACACTGCCA3' {SEQ ID NO:2). Also provided herein is a kit for detecting an APOE3 allele in a nucleic acid sample, comprising the primer pair comprising SEQ ID NO:1 and SEQ ID NO:2 and reagents for detection of nucleic acid.

Certain aspects of the invention are described in greater detail in the non-limiting Example that follows.

EXAMPLES

The present study was conducted in a 16 bed surgical intensive care unit at Duke University Medical Center. Following institutional board approval, written informed consent was obtained from study participants or their legal designates. All consenting adults (age≧18 yrs) who underwent major elective non-cardiac surgery, and who were scheduled to be directly admitted to the surgical intensive care unit (SICU) postoperatively, were eligible for enrollment. Patients who received non-autologous blood transfusions, underwent organ transplantation in the year prior to screening, or did not provide written informed consent were excluded. All prospectively enrolled patients were monitored for development of sepsis daily.

Diagnosis of sepsis syndrome was based on ACCP/SCCM consensus conference criteria (*Crit. Care Med.* 20(6):864-874 (1992)), which requires two or more of the following with infection as the underlying cause: body temperature >38° C. or <36° C., heart rate>90 bpm, respiratory rate>20/min, hyperventilation $PaCO_2$<32 mmHg, and white blood cell count>12,000/$mm^3$ or <4000/$mm^3$ (with immature neutrophils>10%). Sepsis was the primary outcome of interest. Secondary outcomes included length of ICU stay, mortality, and time spent on mechanical ventilation.

Baseline and demographic data were collected on all patients. An Acute Physiologic and Chronic Health Evaluation (APACHE II) score was obtained at study entry (Knaus et al., Crit. Care Med. 13(10):818-829 (1985)). Blood samples were collected in ACD (adenosine-citrate-dextrose) tubes, coded and stored at −80° C. DNA extraction employed a FLEXI GENE DNA system (Qiagen, QI Amp, Valencia, Calif.) to isolate highly purified DNA from whole blood. After extraction, DNA was stored at 4° C. with a chloroform overpass.

A polymerase chain reaction (PCR)-based assay was used to amplify a short polymorphic region residing within coding sequences of the human APOE gene. Each amplification reaction was performed using 20-100 ng of genomic DNA, 1.0 pmol/ml of each primer, 10% dimethylsulfoxide, 1.5 mM $MgCl_2$, 200 mM of each dNTP, 0.05 U/ml Taq DNA polymerase (Promega, Madison, Wis.) and supplied buffer in a final volume of 15 µl. The forward primer was 5' TAAGCT-TGGCACGGCTGTCCAAGGA 3' (SEQ ID NO:1) and the reverse primer was 5' ACAGAATTCGCCCCGGCCTGG-TACACTGCCA 3' (SEQ ID NO:2). An initial denaturation at 94° C. for 5 minutes was followed by 35 cycles of annealing at 65° C. for 0.5 minutes, extension at 70° C. for 45 sec, denaturation at 94° C. for 0.5 minutes, and a final extension at 70° C. for 10 minutes. Following amplification, a 5 µl mixture composed of 2-5 U of the restriction enzyme Hha I (Promega, Madison, Wis.), 2.5 µl of Hha I 10× buffer, and $dH_2O$ to a final volume of 5 µl, was added directly to each well and the reaction incubated for 1-2 hours at 37° C. Resultant DNA fragments were resolved on a 6% nondenaturing polyacrylamide gel via electrophoresis for one hour under constant current (45 mA). DNA fragments were stained with SYBRGREEN (FMC Bioproducts, Rockland, Me.) and visualized using a Storm PhosphorImager and Image Quant™ version 5.0 software (Amersham Biosciences, Piscataway, N.J.). Hha I cleaves the 244 bp PCR product to yield smaller fragments that allow recognition of characteristic patterns following gel electrophoresis. Hha I cuts the APOE3 PCR product to generate 91 bp, 48 bp and 35 bp fragments. The APOE4 allele produces fragments of 72 bp, 48 bp and 35 bp in length, whereas the APOE2 allele generates a 91 bp and 83 bp fragment that appears as a doublet.

A Pearson chi square test was used to test for independence between sepsis status and APOE genotype. In addition to an overall test of independence based on six APOE genotypes present in the sample, three separate one-degree-of-freedom tests were carried out for genotypes defined by the presence or absence of a particular APOE allele (APOE 2, APOE 3, or APOE 4). For each test, a 2×2 table was formed by collapsing APOE genotypes into two groups, consisting of individuals bearing one or two copies of a particular allele and individuals lacking a copy of that allele. For a given APOE allele, this grouping corresponds to a dominant model of gene action. Because some expected cell frequencies were small, an exact p-value based on a permutation distribution rather than an asymptotic chi-square distribution was used to assess statistical significance (Good, Permutation Tests: A Practical Guide to Resampling Methods for Testing Hypothesis, $2^{nd}$ ed. New York, N.Y.: Springer-Verlag (2000)) for all chi square tests.

A Wilcoxon's rank sum test was used to test for differences between genotypes in mortality, length of time in ICU, length of time on mechanical ventilation, and APACHE II score. Relative risks with 95% confidence intervals are reported for genotypes defined by the presence or absence of an APOE allele. Logistic regression was used to access potential effects of age, race, gender and APACHE II score on association between sepsis and APOE genotype. Based on preclinical evidence (Brown et al., Free Radic. Biol. Med. 32(11):1071-1075 (2002); Colton et al., J. Neuroimmunol. 147(1-2):62-67 (2004)), a test was run for interaction between APOE genotype and gender using logistic regression.

All statistical analyses were performed using SAS version 8.02 (SAS Institute, Cary, N.C.). Continuous variables are presented as mean±standard deviation and categorical variables are presented as percentages.

Of 343 patients prospectively enrolled during an 8-month period, 34 (9.9%) developed postoperative severe sepsis. Table 1 presents demographic and clinical characteristics and comorbidities for 34 sepsis patients and 309 patients without sepsis. As expected, mean APACHE II score, days on mechanical ventilation (expressed as days on the ventilator, and as percent of patients on the ventilator) and days in the ICU are higher in patients with sepsis compared with patients without sepsis. Table 2 presents sites of infection and causative organism. Among patients with severe sepsis, 26.5% had a positive blood culture, compared with 3.9% of patients without severe sepsis.

TABLE 1

Summary statistics for patients with and without sepsis

| Characteristic | Sepsis (n = 34) | No sepsis (n = 309) |
|---|---|---|
| Age (years)[a] | 51.9 ± 2.7 | 53.2 ± 0.9 |
| Male (%) | 76 | 54 |
| Caucasian (%) | 71 | 84 |
| Commorbidities (%) | | |
| Hypertension | 29.4 | 35.3 |
| Myocardial Infarction | 5.9 | 4.5 |
| Congestive Heart Failure | 8.8 | 1.9 |
| Diabetes | 8.8 | 11.7 |
| Pancreatitis | 14.7 | 4.5 |
| Liver Disease | 26.5 | 7.4 |
| COPD | 2.9 | 5.2 |
| Cancer | 32.4 | 49.2 |
| Trauma | 14.7 | 20.1 |
| APACHE II Score[a] | 19.7 ± 1.4 | 12.4 ± 0.4 |
| Mechanical Ventilation (%) | 82 | 26 |
| Mechanical Ventilator (Days)[a] | 9.8 ± 1.8 | 2.9 ± 0.9 |
| ICU (Days)[a] | 14 ± 2.3 | 2.2 ± 0.4 |
| Vasopressor Infusion (%) | 20.6 | 1.6 |

[a]mean ± standard error

TABLE 2

Sites of infection and types of organism

| Characteristic | Sepsis (n = 34) | No Sepsis (n = 309) |
|---|---|---|
| Site of Infection (%)[a] | | |
| Lungs | 41.2 | 1.3 |
| Abdomen | 35.3 | 4.2 |
| Urinary Tract | 17.6 | 7.4 |
| Other[b] | 29.4 | 5.4 |
| Type of Organism (%) | | |
| Gram Positive | 61.8 | 9.1 |
| Gram Negative | 44.1 | 9.4 |

TABLE 2-continued

Sites of infection and types of organism

| Characteristic | Sepsis (n = 34) | No Sepsis (n = 309) |
|---|---|---|
| Gram Positive and Gram Negative | 2.9 | 1.9 |
| Fungus | 8.8 | 1.0 |

[a]based on clinical findings
[b]includes blood and tissue, sinus, bone, and CSF The distribution of APOE for patients with sepsis and patients without sepsis is given in Table 3. The hypothesis of independence for this table is rejected by a Pearson chi-square test (5 df, p=0.015). Collapsing APOE genotypes into two groups based on the presence or absence of a specified APOE allele results in three 2×2 tables. Tests of independence for genotypes based on APOE 2, APOE 3 or APOE 4 yielded p values of 0.138, 0.014, and 1.00, respectively. Consequently, genotypes based on the presence of the APOE 3 allele are not independent of sepsis. Presence of at least one copy of the APOE3 allele was associated with significantly reduced incidence of severe sepsis (p=0.014). In contrast, genotypes based on the presence of APOE2 (p=0.138) or APOE4 (p=1.0) alleles were not associated with incidence of severe sepsis. The magnitude of genotypic effect in these data is illustrated in FIG. 1, which shows estimates of the probability of sepsis based on allele-specific APOE genotypes.

TABLE 3

Distribution of APOE genotypes in patients with and without sepsis.
($\chi^2$ = 16.85, 5 df, p = 0.015)

| | APOE Genotype | | | | | |
|---|---|---|---|---|---|---|
| | E2/E2 | E2/E3 | E2/E4 | E3/E3 | E3/E4 | E4/E4 |
| Sepsis Absent | 0 | 42 | 5 | 180 | 76 | 6 |
| Sepsis Present | 1 | 5 | 3 | 18 | 6 | 1 |

Figure 2:
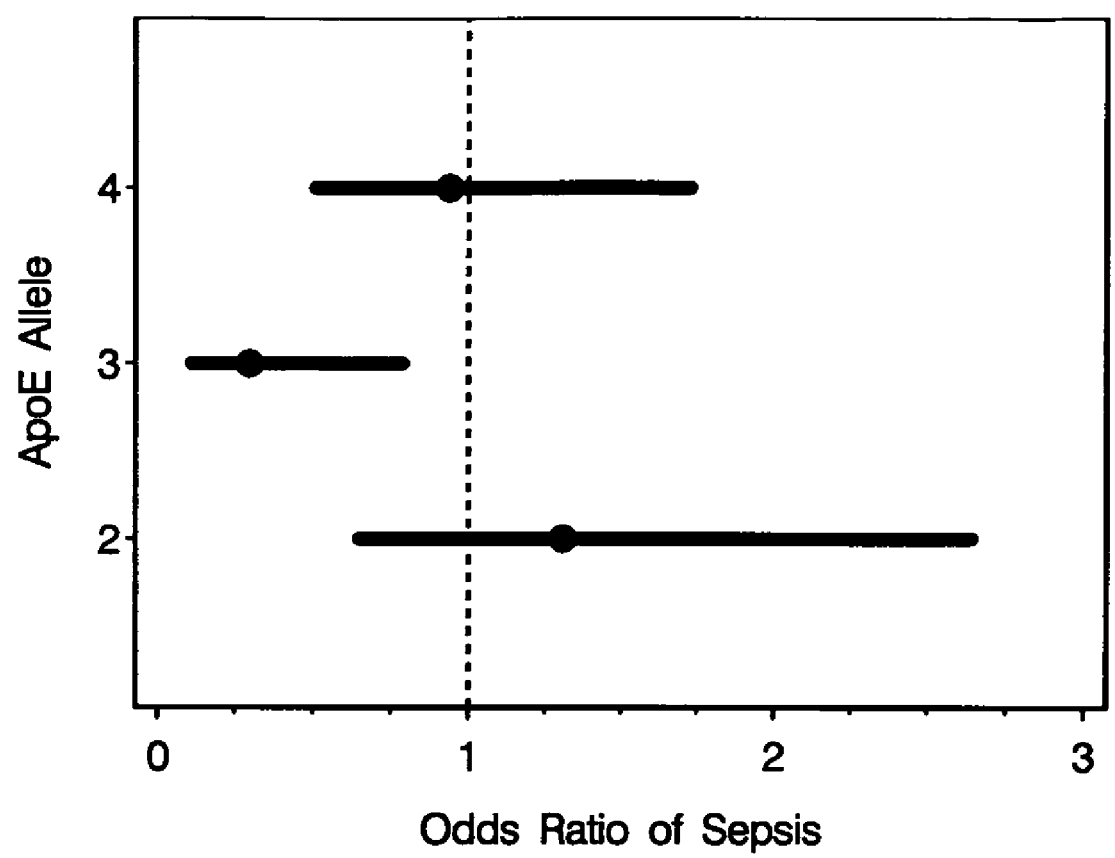
FIG. 2. Odds ratios for carriers of APOE alleles 2, 3 and 4. The odds ratio is the ratio of odds of sepsis for carriers of at least one copy of an APOE allele to the odds of sepsis with no copies of that APOE allele. An odds ratio less than 1 indicates the genotypes carrying the allele have lower risk of sepsis. The bar extends from the lower to the upper 95% confidence limit of odds ratio with the point estimate indicated by a dot.

Odds ratios (OR) and 95% confidence intervals (CI) for genotype bearing one or two copies of APOE 2, APOE 3 or APOE 4 are presented in FIG. 2. The APOE3 allele has an OR of 0.295 (95% CI; 0.110-0.795). The observation that the point estimate of the ratio of odds of sepsis for carriers of at least one copy of APOE3 relative to the odds of sepsis with no copies of the APOE allele 3 is less than 1, indicates that the APOE3 allele is associated with a lower incidence of sepsis.

The effect of APOE3 genotype remained significant in logistic regression models relating sepsis incidence to APOE genotype and individual covariates of age, sex, race and APACHE II score. P values for the effect of APOE3 genotype were 0.007, 0.004, 0.008 and 0.03 with age, sex, race, and APACHE II score in the model, respectively.

Figure 3:
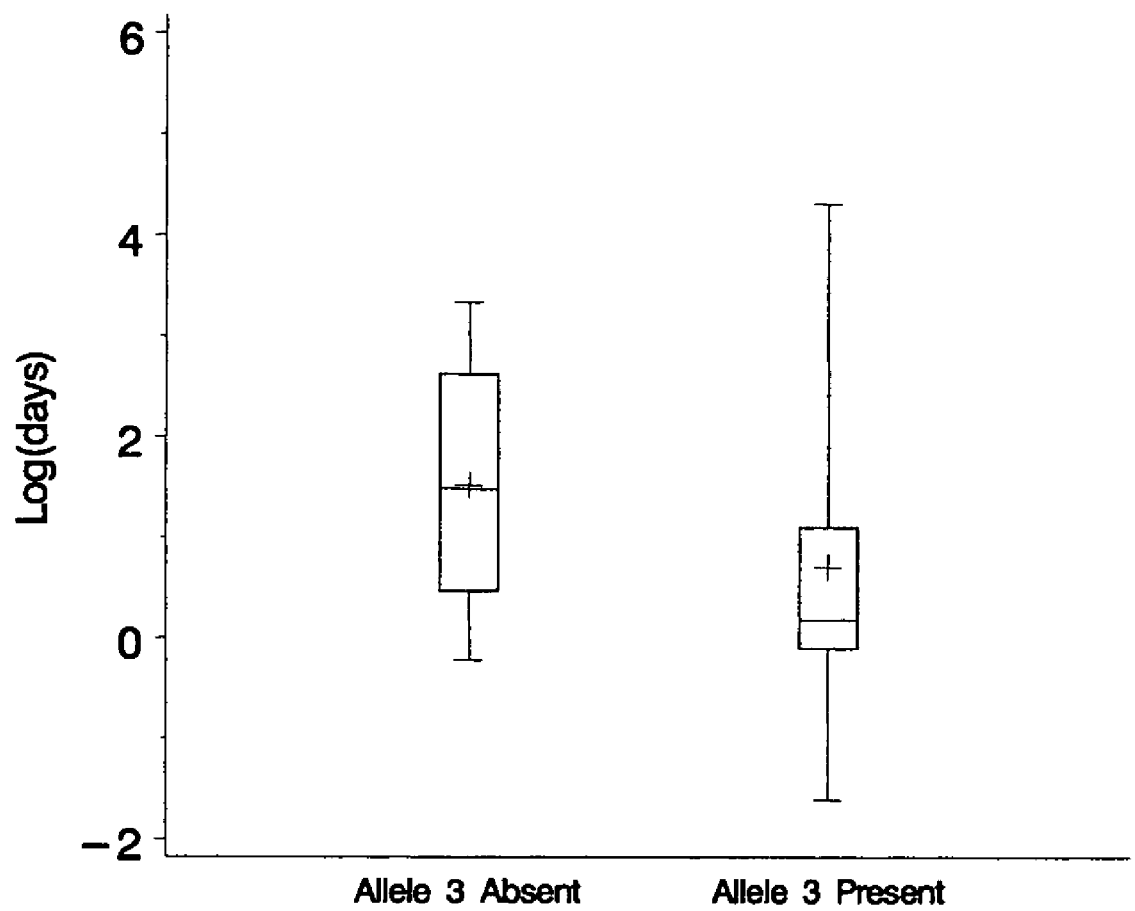
FIG. 3. Box plots displaying length of ICU stay for patients with 1 or 2 copies of the APOE 3 allele (Allele 3 Present) and patients lacking the APOE 3 allele (Allele 3 Absent). The presence of the APOE 3 allele was associated with a shorter length of ICU stay (p=0.02)

To determine whether a lower incidence of sepsis translates into other clinical benefits, length of ICU stay and other clinical parameters were next examined. Length of ICU stay, evaluated as a secondary endpoint, was also found to be correlated with APOE genotype, with the presence of the APOE3 allele significantly associated with shorter ICU stay (p=0.02; FIG. 3). Although patients with the APOE3 allele had a lower median duration of mechanical ventilation and lower APACHE II score, this did not achieve statistical significance. The odds ratio for mortality with respect to presence of APOE3 was 0.858 (95% CI 0.108-6.828), suggesting that APOE3 was protective. A test for interaction between APOE3 genotype and gender was not significant (p=0.07).

In summary, this study demonstrates that APOE genotype influences susceptibility to severe sepsis in an isoform-specific fashion. In particular, the presence of the APOE3 allele is associated with significant reduction in incidence of post-operative severe sepsis in a cohort of patients undergoing elective noncardiac surgery.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference into this application in order to more fully describe the state of the art to which this invention pertains.

What is claimed is:

1. A method of identifying a human subject having a decreased risk of developing sepsis, comprising detecting at least one copy of an apolipoprotein E3 (APOE3) allele in nucleic acid of the subject, wherein the detection of at least one copy of an APOE3 allele in nucleic acid of the subject identifies the subject as having a decreased risk of developing sepsis.

2. The method of claim 1, wherein the subject is a perioperative patient.

3. The method of claim 1, wherein the subject is a periprocedural patient.

4. The method of claim 1, wherein the subject is an intensive care unit patient.

5. The method of claim 1, wherein the detecting step is carried out prior to surgery on the subject.

6. The method of claim 1, wherein the detecting step is carried out prior to the performance of an invasive procedure on the subject.

7. The method of claim 1, wherein the subject has developed sepsis.

8. The method of claim 1, wherein the subject has a relative who has developed sepsis.

9. The method of claim 1, wherein detecting at least one copy of an APOE3 allele is carried out by an amplification reaction.

10. The method of claim 9, wherein the amplification reaction is carried out with a primer pair consisting of a first oligonucleotide comprising the nucleotide sequence of SEQ ID NO:1 and a second oligonucleotide comprising the nucleotide sequence of SEQ ID NO:2.

11. The method of claim 1, wherein detecting at least one copy of an APOE3 allele is carried out by a hybridization reaction.

12. The method of claim 11, wherein the hybridization reaction is carried out with hybridization probes attached to a solid support.

13. The method of claim 1, wherein detecting at least one copy of an APOE3 allele is carried out by sequencing nucleic acid of the subject.

14. The method of claim 1, wherein detecting at least one copy of an APOE3 allele is carried out by restriction fragment length polymorphism analysis.

15. The method of claim 1, wherein detecting at least one copy of an APOE3 allele is carried out by high performance liquid chromatography.

16. The method of claim 1, wherein detecting at least one copy of an APOE3 allele is carried out by a ligase chain reaction.

* * * * *

UNITED STATES PATENT AND TRADEMARK OFFICE
CERTIFICATE OF CORRECTION

PATENT NO. : 7,592,141 B2
APPLICATION NO. : 11/302064
DATED : September 22, 2009
INVENTOR(S) : Schwinn et al.

It is certified that error appears in the above-identified patent and that said Letters Patent is hereby corrected as shown below:

Col. 2, Line 6: Please correct "$Arg_{58}$" to read -- $Arg_{158}$ --.

Signed and Sealed this

Second Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,592,141 B2  Page 1 of 1
APPLICATION NO. : 11/302064
DATED : September 22, 2009
INVENTOR(S) : Schwinn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 421 days.

Signed and Sealed this

Twenty-first Day of September, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 25
<212> TYPE: DNA
<213> ORGANISM: Artificial
<220> FEATURE:
<223> OTHER INFORMATION: Oligonucleotide primer

<400> SEQUENCE: 1
taagcttggc acggctgtcc aagga                                           25

<210> SEQ ID NO 2
<211> LENGTH: 31
<212> TYPE: DNA
<213> ORGANISM: Artificial
<220> FEATURE:
<223> OTHER INFORMATION: Oligoncucleotide primer -continued

```
<400> SEQUENCE: 2
acagaattcg ccccggcctg gtacactgcc a                                           31
```